United States Patent [19]
Izoret

[11] Patent Number: 6,007,613
[45] Date of Patent: Dec. 28, 1999

[54] BIOADHESIVE; PREPARATION PROCEDURE AND DEVICE FOR THE APPLICATION OF A BIOADHESIVE; AND HARDENERS FOR A BIOADHESIVE

[75] Inventor: Georges Izoret, Sevres, France

[73] Assignee: Fusion Medical Technologies, Inc., Mountain View, Calif.

[21] Appl. No.: 08/860,769

[22] PCT Filed: Oct. 27, 1995

[86] PCT No.: PCT/FR95/01420

§ 371 Date: Nov. 28, 1997

§ 102(e) Date: Nov. 28, 1997

[87] PCT Pub. No.: WO96/14368

PCT Pub. Date: May 17, 1996

[30] Foreign Application Priority Data

Nov. 3, 1994 [FR] France .................... 94 13136

[51] Int. Cl.$^6$ .............. C08L 89/00; C08L 1/08; C08L 5/11
[52] U.S. Cl. ................. 106/160.1; 106/140.1; 106/144.1
[58] Field of Search ............ 106/160.1, 140.1, 106/144.1

[56] References Cited

U.S. PATENT DOCUMENTS

| | | | |
|---|---|---|---|
| 3,758,660 | 9/1973 | Battista | 264/202 |
| 3,917,862 | 11/1975 | Bridgeford | 426/105 |
| 4,187,119 | 2/1980 | Battard et al. | 106/144.1 |
| 4,292,028 | 9/1981 | Barr | 106/35 |
| 4,329,333 | 5/1982 | Barr | 429/19 |
| 4,394,370 | 7/1983 | Jefferies | 606/76 |
| 4,749,689 | 6/1988 | Miyata et al. | 514/21 |
| 5,129,882 | 7/1992 | Weldon et al. | 604/96 |
| 5,292,333 | 3/1994 | Johnson | 606/214 |
| 5,330,446 | 7/1994 | Weldon et al. | 604/271 |
| 5,336,616 | 8/1994 | Livesey et al. | 435/395 |
| 5,385,606 | 1/1995 | Kowanko | 527/205 |
| 5,418,222 | 5/1995 | Song et al. | 514/21 |
| 5,507,744 | 4/1996 | Tay et al. | 606/50 |
| 5,597,897 | 1/1997 | Ron et al. | 530/350 |
| 5,607,590 | 3/1997 | Shimizu | 210/490 |
| 5,618,312 | 4/1997 | Yui et al. | 606/229 |
| 5,755,778 | 5/1998 | Kleshinsky | 606/153 |

FOREIGN PATENT DOCUMENTS

WO 92/22252  12/1992  WIPO .

*Primary Examiner*—Peter A. Szekely
*Attorney, Agent, or Firm*—Townsend and Townsend and Crew LLP

[57] ABSTRACT

The present invention relates to a bioadhesive that includes at least two constituents that are intended to be combined, for simultaneous, separate, or time-shifted use, i.e.: 1) a semi-liquid constituent (A) that includes, at a minimum, gelatin in an aqueous solution; and 2) A constituent (B), in gel or non-gel form, that includes, at a minimum, an aldehyde, with the exception of non-gel solutions consisting of formaldehyde, glutaraldehyde, or glyceraldehyde. The invention also relates to the use of succinic dialdehyde and of aldehyde solution sin gel form as hardeners in a bioadhesive, and further relates to a procedure for the preparation of the said bioadhesives and to a device for the application of the said bioadhesives.

5 Claims, No Drawings

BIOADHESIVE; PREPARATION PROCEDURE AND DEVICE FOR THE APPLICATION OF A BIOADHESIVE; AND HARDENERS FOR A BIOADHESIVE

The present invention relates to bioadhesives having a gelatin base and an aldehyde hardener; to a procedure for preparing the bioadhesives and to a device for their application; and also to hardeners for such adhesives.

The use of adhesives having a base of gelatin and resorcinol, hardened by an aldehyde (known generally as "GRA adhesives"), is known in the field of human and animal surgery, and particularly in the field of vascular surgery. More specifically, the use of GRF (gelatin-resorcinol-formol) adhesives has often been described in connection with the gluing of tissues (cf. *RBM*, Vol. 4, No. 2 (March/April 1982), page 147, and *Nouvelle Presse Médicale*, Vol. 4, No. 10 (Mar. 8, 1975).

The gelatin was selected primarily because of its innocuousness and because of its hemostatic properties, and also because of its ability to react with certain aldehydes, known as "hardeners". in order to form, by reticulation, an adhesive mass. The resorcinol also makes it possible to strengthen the quality of this type of adhesion.

The use of certain aldehydes (such as 37 percent officinal formol, 25 percent glutaraldehyde, or even a mixture of the latter two aldehydes in 9:1 ratio) is known; however, these aldehydes are utilized only in non-gel solution. These aldehydes have the disadvantage of being toxic at such concentrations (with an $LD_{50}$ of 296 mg/kg for the formaldehyde and an $LD_{50}$ of 33.7 mg/kg for the glutaraldehyde).

The use of such GRF adhesives requires that the surgeon first spread the gelatin/resorcinol (GR) mixture over the dry surfaces of the organ to be glued; then spray, instill, or deposit by small drops, with the aid of an intradermal syringe, the liquid hardener (i.e., the stabilized aqueous formaldehyde solution) onto the GR mixture; and finally apply the adhesive-coated surfaces to one another (cf. the CNIMH files, Vol. 6 (November–December 1984)). It is known that aqueous solutions of formaldehyde, glutaraldehyde, and glyceraldehyde, or mixtures thereof, can be utilized as liquid hardening agents.

This method requires a high degree of precision on the part of the surgeon, particularly because of the necrotic effect of the formol. In fact, the aspersion of formol onto living tissue not involved in the adhesive procedure causes damage and necroses that are often irreversible. Up till now, the surgical technique has consisted of very carefully protecting the adjacent tissue; however, these precautions often turn out to be insufficient. Furthermore, the risk of the surgeon's pricking himself with a syringe full of formol is always present; and, even at very low doses, an injection of formol causes a shock to the practitioner, who may therefore be required to interrupt the operation.

The present applicants have now developed a bioadhesive that remedies the major disadvantages of the known adhesives as described hereinabove.

Accordingly, the present invention relates to a bioadhesive that includes at least two constituents that are intended to be combined, for simultaneous, separate, or time-shifted use, i.e.:

1) A semi-liquid constituent (A) that includes, at a minimum, gelatin in an aqueous solution; and 2) A constituent (B), in gel or non-gel form, that includes, at a minimum, an aldehyde, with the exception of non-gel solutions consisting of formaldehyde, glutaraldehyde, or glyceraldehyde.

In a preferred embodiment of the invention, the constituent (B) is in gel form, and the disadvantages described hereinabove are avoided, in accordance with the invention, because hardeners in gel form are easier to handle than liquid hardeners, and prevent the risks of inadvertent aspersions and the consequent necroses, and do not require the use of the same syringes. The said adhesives are applied in connection with the gluing of human or animal tissues, and particularly in connection with the gluing of arteries and aortas.

The first constituent (A) is customarily utilized in GRA adhesives. It consists of an aqueous solution of gelatin in semi-liquid form. It may contain from 5 to 20 grams of gelatin for every 20 to 25 ml of distilled water. The semi-liquid GR constituent usually contains approximately 15 grams of gelatin for every 20 ml of distilled water.

The aqueous gelatin solution may also contain resorcinol or phloroglucinol, in the form of a mixture with the gelatin. Usually, approximately 4 to 6 grams of resorcinol or phloroglucinol are used for every 20 to 25 ml of water, and the solution preferably contains approximately 5 grams of resorcinol for approximately 15 grams of gelatin and approximately 20 ml of water. Because the resorcinol is not non-toxic, an adhesive that contains only a little resorcinol, or none at all, may be useful.

In accordance with a preferred embodiment of the invention, the constituent (B), which includes the hardening aldehyde, is in gel form, and preferably in the form of an aqueous gel. The gelling agents that can be utilized include all of the customary, currently available, and biologically acceptable gelling agents that do not reach with the aldehydes. The gelling agents that can be utilized include, in particular, agar-agar, karaya gum, silica powders, and the hydroxylated and carboxylated derivatives of cellulose, such as hydroxyethyl cellulose, carboxymethyl cellulose, and mixtures thereof.

In accordance with the invention, the aldehydes that can be utilized are selected from among officinal formaldehyde, glutaraldehyde, glyceraldehyde, succinic dialdehyde, sulfonyl-bis-acetaldehyde, 1,8-octanedial 4-octene 1,8-dial, oxy-bis-acetaldehyde, and mixtures of these aldehydes.

In the second constituent (B) in gel form, the customary aldehydes are utilized at their customary concentrations for liquid hardeners, and may optionally be in the form of mixtures, as in liquid hardeners. The preferred aldehyde is succinic dialdehyde, whose utilization as a hardener for bioadhesives has not yet been described. This aldehyde is effective at very low concentrations, on the order of 5 percent by weight of the hardener, thereby providing an advantage in view of the toxicity of the aldehydes.

Among the mixtures, preference is given to mixtures of succinic dialdehyde and glutaraldehyde (in a ratio of 5:0.25).

The customary concentrations of aldehyde in liquid hardeners may reach values on the order of 1 to 50 percent by weight of aldehyde, and, typically, from 1 to 40 percent by weight for glutaraldehyde and from 1 to 50 percent by weight for oxy-bis-acetaldehyde.

For succinic dialdehyde, the concentrations may range from 1 to 40 percent, and preferably from approximately 5 to 20 percent.

Whereas the customary mixture consists of formol and glutaraldehyde (9 parts by volume of 37-percent formol for 1 part of 40-percent glutaraldehyde), the succinic dialdehyde mixture contains, by weight in constituent (B), from 40 to 50 percent succinic dialdehyde and from 0.2 to 1 percent glutaraldehyde.

The gelling agent is optionally utilized, in an aqueous solution, in proportions on the order of 1 to 5 percent by weight, and preferably 2 percent by weight. This proportion depends, on the one hand, on the gelling agent utilized, and, on the other hand, on the viscosity of the semi-liquid constituent (A). In fact, during application, it may be useful for the constituents (A) and (B) to have similar viscosities.

The invention also relates to aqueous solutions, in gel form, of the said aldehydes or mixtures thereof, which solutions may optionally be stabilized, and which are useful particularly as hardeners for bioadhesives.

The aldehyde gels obtained with the said products are stable at room temperature for at least one year. Furthermore, the initial aldehyde content is maintained throughout the said period.

The invention also relates to the use of succinic dialdehyde as a hardener for bioadhesives. The bioadhesives that can be hardened by such a succinic dialdehyde, in an aqueous solution or in an aqueous solution in gel form, include, on the one hand, a semi-liquid constituent that includes, at a minimum, gelatin, and optionally resorcinol or phloroglucinol, and, on the other hand, an aldehyde constituent, in liquid or gel form, that includes at a minimum, as a hardener, succinic dialdehyde. The dialdehyde may optionally be mixed with another hardening aldehyde. In view of its high degree of effectiveness, this dialdehyde is particularly well suited to use in gluing the liver, lung, spleen, pericardium, and kidney. Its effectiveness makes it possible to reduce the percentage of aldehyde utilized, to approximately 5 percent by weight in constituent (B).

In the said bioadhesives that contain succinic dialdehyde, the succinic dialdehyde (whether or not it is utilized in constituent (B)) is utilized at concentrations ranging from approximately 1 to 40 percent, and preferably from 5 to 20 percent, by weight.

The present invention also relates to a procedure for the preparation of a bioadhesive, characterized by the fact that, on the one hand, a semi-liquid constituent (A) that includes, at a minimum, gelatin in an aqueous solution, and, on the other hand, a constituent (B) that includes, at a minimum, one aldehyde, with the exception of non-gel solutions consisting of formaldehyde, glutaraldehyde, or glyceraldehyde, are mixed and applied in the form of superimposed layers.

The two constituents are preferably mixed immediately prior to use.

To prepare the adhesive, the semi-liquid constituent (A) is prepared, on the one hand, by diluting the gelatin (and, optionally, the resorcinol) in distilled water and, on the other hand, by introducing the aldehyde (and, optionally, the gelling agent) into the water.

When the adhesive is ready for use, constituent (A) is customarily pre-heated, in a water-bath, to a temperature on the order of 28 to 40 degrees [Celsius], and preferably to a temperature on the order of 37 degrees [Celsius].

In accordance with the invention, the aldehyde gels are utilized at room temperature, but may also be utilized at temperatures on the order of human temperature, i.e., temperatures on the order of 28 to 40 degrees [Celsius].

The use of hardeners in gel form makes it possible to utilized a device consisting of a syringe of the type with two bodies, or any other means that are appropriate for mixing and quantifying, in appropriate proportions, constituent (A) and constituent (B) containing the selected aldehyde at the concentration that is most appropriate for the type of gluing in question.

This operational procedure frees the surgeon from the need to create the mixture himself extemporaneously, or to apply the adhesive in two steps. The result is not only a saving in terms of time, but also a better quantification of the constituents, and, finally, avoidance of the risk of erroneously applying the hardener to the tissues adjacent to the tissues to be glued.

Furthermore, for the application of constituent (B) in non-gel form, it is possible first to apply constituent (A) in the form of a layer on at least one of the surfaces of the tissues to be glued, and then to inject constituent (B) into the said layer before applying the tissues to one another.

Thus, the invention relates to a device having two compartments, one of which contains constituent (A) and the other of which contains constituent (B), as defined hereinabove.

A suitable device consists of a syringe of the type with two bodies, one of whose bodies contains a constituent (A), which includes, at a minimum, gelatin in an aqueous solution, and whose other body contains a constituent (B), in gel form or in non-gel form, in accordance with the present invention, which includes at least one aldehyde.

In a particular embodiment of the invention, a syringe with two bodies is utilized that allows the simultaneous application of the two components, or the immediate mixture of the two components at the outlet of the syringe.

Dual-body syringes of this type are known under the trade name "Duploject".

Preferably, and particularly in this mode of application, constituents (A) and (B) are utilized whose viscosities are similar.

The bioadhesives prepared in accordance with the invention have been shown to be particularly effective, especially in connection with aortic gluing and in connection with the gluing of the pericardium, lung, liver, spleen, and kidney. Generally speaking, the adhesives in accordance with the invention can be utilized in bone, vascular, visceral, and dental surgery.

The following examples provide illustrations of the invention, without however limiting its scope.

EXAMPLE 1

Constituent (A)

A GR paste is obtained through the dissolution, in 20 to 25 ml of distilled water, kept at a temperature of 50 degrees C. in a water-bath, of 2 grams of a mixture of resorcinol and powdered gelatin, in proportions of ¼ and ¾, respectively. The proper consistency of the mixture is obtained within 30 minutes, through the use of a planetary stirring device that is operated slowly in order to prevent the formation of air-bubbles.

Constituent (B)

One volume consisting of an aqueous solution of glutaraldehyde (25 percent by weight) is added to 9 volumes of an aqueous solution of formol (37 percent by weight), followed by 1.5 to 2 by weight of hydroxyethyl cellulose. The resulting mixture is heated, under mechanical stirring, in a water-bath until the hydroxyethyl cellulose is completely dissolved. After cooling to room temperature, a gel is obtained whose viscosity is similar to that of the GR mixture. The resulting viscosity is a function of the quantity of hydroxyethyl cellulose utilized. The percentage indicated in the present example is not limitative.

The mixture of constituents (A) and (B) is applied to the tissues to be glued, and the said tissues are applied to one another.

EXAMPLE 2

Constituent (A)

A pre-constituted GR paste is utilized, as obtained from the gelatin-resorcinol-water mixture described in Example 1 above. The said paste is placed in a sterile tube ready for use, after heating for 5 to 10 minutes, in a sterile water-bath at a temperature of 45 degrees C.

Constituent (B)

A quantity of carboxymethyl cellulose (2 percent by weight) is added to an aqueous solution containing succinic dialdehyde (5 percent by weight) and glutaraldehyde (0.25 percent by weight). The resulting mixture is heated and stirred in the same way as in Example 1 above until a gel (B) is obtained.

The mixture consisting of constituents (A) and (B) is applied to the tissues to be glued, and the said tissues are applied to one another.

EXAMPLE 3

The same procedure described in Example 2 above is followed, but with the use of a 5-percent aqueous solution of succinic dialdehyde, and with no glutaraldehyde, as constituent (B).

The mixture consisting of constituents (A) and (B) is applied to the tissues to be glued, and the said tissues are applied to one another.

EXAMPLE 4

Constituent (A) is the same as in Example 1 above.

An aqueous gel is prepared that contains 36 percent by weight of formaldehyde, 4.5 percent by weight of succinic dialdehyde, and 2 percent by weight of carboxymethyl cellulose. The resulting mixture is heated and stirred in the same way as in Example 1 above until a gel (B) is obtained.

The mixture consisting of constituents (A) and (B) is applied to the tissues to be glued, and the said tissues are applied to one another.

EXAMPLE 5

Constituent (A)

This constituent is identical to the one in Example 1 above.

Constituent (B)

An aqueous solution containing succinic dialdehyde (20 percent by weight) is utilized.

A layer of constituent (A) is applied to the tissues to be glued. Then solution (B) is injected into the layer of constituent (A). The tissues to be glued are then applied to one another.

I claim:

1. A bioadhesive composition comprising:

a first constituent including an aqueous solution of gelatin; and a second constituent maintained separately from the first constituent and including succinic dialdehyde present in an amount sufficient to promote cross-linking of the gelatin in the first constituent;

wherein the first and second constituents may be combined and applied to tissue as an adhesive.

2. A bioadhesive composition as in claim 1, wherein the second constituent is a gel.

3. A bioadhesive composition as in claim 2, wherein the second constituent comprises a gelling agent selected from the group consisting of agar, karaya gum, silica powder, hydroxyethyl cellulose, carboxymethyl cellulose, hydroxylated cellulose, and carboxylated cellulose.

4. A bioadhesive composition as in any one of claims 1–3, wherein the aqueous solution of gelatin includes from 5 g to 20 g of gelatin for every 20 ml to 25 ml of water.

5. A bioadhesive composition as in any one of claims 1–3, wherein the second constituent comprises from 1% by weight to 40% by weight succinic dialdehyde.

* * * * *